United States Patent
Lan et al.

(10) Patent No.: US 11,202,847 B1
(45) Date of Patent: Dec. 21, 2021

(54) GERMICIDAL PANEL LIGHT

(71) Applicant: SHENZHEN GUANKE TECHNOLOGIES CO., LTD, Shenzhen (CN)

(72) Inventors: Qing Lan, Shenzhen (CN); Tianlong Dai, Shenzhen (CN); Ligen Liu, Shenzhen (CN); Shoubao Chen, Shenzhen (CN)

(73) Assignee: SHENZHEN GUANKE TECHNOLOGIES CO., LTD, Shenzhen (CN)

( * ) Notice: Subject to any disclaimer, the term of this patent is extended or adjusted under 35 U.S.C. 154(b) by 0 days.

(21) Appl. No.: 17/023,898

(22) Filed: Sep. 17, 2020

(30) Foreign Application Priority Data

Aug. 13, 2020 (CN) .......................... 202021693509.6

(51) Int. Cl.
*A61L 9/20* (2006.01)
(52) U.S. Cl.
CPC ............. *A61L 9/20* (2013.01); *A61L 2209/12* (2013.01); *A61L 2209/14* (2013.01); *A61L 2209/15* (2013.01)
(58) Field of Classification Search
None
See application file for complete search history.

(56) References Cited

U.S. PATENT DOCUMENTS

| | | | | |
|---|---|---|---|---|
| 4,416,748 A | * | 11/1983 | Stevens | B01D 53/60 204/157.3 |
| 6,053,968 A | * | 4/2000 | Miller | F24F 8/22 96/224 |
| 7,498,009 B2 | * | 3/2009 | Leach | B01D 53/007 204/157.3 |
| 2001/0048889 A1 | * | 12/2001 | Palestro | A61L 9/20 422/4 |
| 2004/0141875 A1 | * | 7/2004 | Doshi | A61L 9/20 422/4 |
| 2004/0184949 A1 | * | 9/2004 | McEllen | A61L 9/20 422/4 |
| 2005/0047975 A1 | * | 3/2005 | Tang | A61L 9/20 422/121 |
| 2006/0177356 A1 | * | 8/2006 | Miller | A61M 11/06 422/121 |
| 2008/0152548 A1 | * | 6/2008 | Clark | A61L 9/205 422/121 |

(Continued)

*Primary Examiner* — Andrew Smyth
(74) *Attorney, Agent, or Firm* — Maier & Maier, PLLC

(57) ABSTRACT

A germicidal panel light includes a housing, a sterilization component, a fan component and a lighting component; the housing provided with a mounting cavity as well as an air inlet and an air outlet connecting to the mounting cavity, inner wall of the mounting cavity forming an air guiding plane corresponding to the air inlet and the air outlet respectively, the appearance of the housing provided with a containing groove whose inner wall is provided as a reflecting surface; the sterilization component is provided in the mounting cavity; the fan component is provided in the mounting cavity and is provided at intervals with the sterilization component; and the lighting component is provided in the containing groove. The germicidal panel light has an air guiding plane in the mounting cavity nearby the air inlet, so air can be guided into the mounting cavity, air flows slowly, and noises are reduced.

11 Claims, 7 Drawing Sheets

(56) References Cited

U.S. PATENT DOCUMENTS

| | | | |
|---|---|---|---|
| 2008/0279733 A1* | 11/2008 | Glazman | F24F 8/192 422/186.3 |
| 2015/0352242 A1* | 12/2015 | Ando | A61L 9/205 422/122 |
| 2016/0033148 A1* | 2/2016 | Darvill | F24F 8/192 210/143 |
| 2016/0325606 A1* | 11/2016 | Kim | A61L 9/205 |
| 2018/0347574 A1* | 12/2018 | Niemiec | F21S 10/06 |
| 2019/0072288 A1* | 3/2019 | Niemiec | F21V 33/0096 |
| 2019/0113219 A1* | 4/2019 | Niemiec | A01M 1/08 |
| 2019/0292315 A1* | 9/2019 | Niemiec | A61L 9/20 |
| 2020/0108166 A1* | 4/2020 | Rhoden | B01D 46/10 |
| 2020/0116163 A1* | 4/2020 | Niemiec | F04D 29/547 |
| 2020/0354513 A1* | 11/2020 | Niemiec | F04D 25/088 |

* cited by examiner

GERMICIDAL PANEL LIGHT

CROSS-REFERENCE TO RELATED APPLICATIONS

The present patent application claims benefit and priority to Chinese Application No. 2020216935096 filed on Aug. 13, 2020, which is hereby incorporated by reference into the present disclosure.

FIELD

The embodiments relate to the field of germicidal equipment, particularly to a germicidal panel light.

BACKGROUND

The UV germicidal panel light can be used for air sterilization. Its sterilization principle is that air is sucked into the light for UV irradiation and then is exhausted outside the light. During the sterilization process, negative pressure is generated inside the UV germicidal panel light, and then air flows quickly into the UV germicidal panel light, strong air convection is generated at the air inlet, and then noises are generated. In another aspect, the working power of the fan can be improved to speed up the flowing speed of incoming and outgoing air and improve the air sterilization efficiency. When the working power of the fan is improved, the air speed at the air inlet is accelerated, so high noises are generated.

The foregoing content is only used for assisting in understanding the technical scheme of the invention, but not mean the acknowledgement of that the above content is a prior art.

SUMMARY

An main object of the embodiments is to provide a germicidal panel light to reduce noises generated during working of the UV germicidal panel light.

To realize the above objective, the germicidal panel light according to the utility model comprises:

a housing provided with a mounting cavity as well as an air inlet and an air outlet connecting to said mounting cavity, inner wall of said mounting cavity forming a air guiding plane corresponding to said air inlet and said air outlet respectively, the appearance of said housing provided with a containing groove whose inner wall is provided as a reflecting surface;

a sterilization component provided in said mounting cavity;

a fan component is provided in said mounting cavity and is provided at intervals with said sterilization component; and a lighting component provided in said containing groove.

In one embodiment of this utility model, said germicidal panel light also comprises an air inlet grille and an air outlet grille connecting to said housing;

said air inlet grille covers said air inlet; and said air outlet grille covers said air outlet.

In one embodiment of this utility model, said air inlet grille is provided with several air guiding vents, and the air incoming direction of each of said air guiding vents faces the air guiding plane of nearby said air inlet.

In one embodiment of this utility model, said fan component is provided corresponding to said air outlet, and said fan component is a centrifugal fan.

In one embodiment of this utility model, said air inlet, said mounting cavity and said air outlet cooperate to form an air duct;

said germicidal panel light also comprises a filter component connecting to the inner wall of said mounting cavity, said filter component covers said air duct and is provided nearby said air inlet.

In one embodiment of this utility model, said sterilization component is a UV fluorescent tube;

the inner wall of the said mounting cavity is provided as a reflecting surface.

In one embodiment of this utility model, said germicidal panel light also comprises several lifting lugs which connect to the peripheral wall of said housing.

In one embodiment of this utility model, said housing is provided with mounting holes which are provided at intervals with said air inlet, said air outlet and said containing groove;

said germicidal panel light also comprises a display module provided in said mounting cavity and corresponding to said mounting hole.

In one embodiment of this utility model, said housing comprises:

bottom housing; and front housing, said front housing and said bottom housing connect to each other and enclose each other, forming said mounting cavity, said front housing is provided with said air outlet and said air inlet, said air outlet and said air inlet are provided nearby two facing sides of said front housing respectively, the middle part of said front housing sink towards said mounting cavity, forming two said air guiding planes and said containing groove;

said sterilization component and said fan component connects to said front housing and/or said bottom housing.

In one embodiment of this utility model, said bottom housing comprises a housing body and a back housing, said housing body is provided with said mounting groove and offsetting holes connecting the bottom wall of said mounting groove, said back housing connects to said housing body and covers said offsetting hole;

said front housing connects to said housing body and covers the notch of said mounting groove.

In one embodiment of this utility model, said containing groove is uncovered, two facing side walls of said containing groove are provided with a convex part for locating, each of said convex parts for locating works with the wall of said containing groove, forming a locating groove in the way of spacing;

said lighting component comprises a lighting module and a lampshade, said lighting module connects to the bottom wall of said containing groove and is between two said convex parts for locating, two sides of said lampshade are provided with a fastening part contained partially in said locating groove and cooperating with the locating part of said convex part for locating.

In the utility model, a mounting cavity as well as an air inlet and air outlet connecting the mounting cavity are provided inside the housing, the fan component and the sterilization component are provided inside the mounting cavity at intervals, negative pressure is generated inside the mounting cavity when the fan component works, so that air enters the mounting cavity from the air inlet and exhausted from the air outlet. Wherein, an air guiding plane nearby the air inlet is formed on the inner wall of the mounting cavity, when air flows into the mounting cavity from the air inlet, air is guided by the air guiding plane, so that air can flow into the mounting cavity slowly, which reduces noises generated.

The equipment is characterized by large air volume but low noises. In the meanwhile, the air outlet is provided with an air guiding plane, which can guide air out slowly, reducing generation of noises. In another aspect, the appearance of the housing is provided with a containing groove where the lighting component is provided, so that the inner wall of the containing groove reflects the ray of light of the lighting component to recycle ray of light, a lighting area where the luminance is lower than the body of the lighting component is formed in the containing groove, so that dazzle caused by the lighting component is reduced, the lighting quality of the germicidal panel light is improved, and the lighting cost is saved. In yet another aspect, the appearance of the housing is provided with a containing groove in which the lighting component is provided to reduce the height of the lighting component out of the surface of the housing, reduce the overall thickness of the germicidal panel light and reduce the dimension of the germicidal panel light. In addition, the lighting component is provided in the containing groove, reducing the dimension of the lighting component and saving the cost of the lighting component.

BRIEF DESCRIPTION OF THE DRAWINGS

To better describe the technical schemes of the embodiments of utility model or prior art, a brief introduction of FIG. to be used in the descriptions of the embodiment or prior art is made hereby. Obviously, the Attached Figure described below are only several embodiments of the utility model. For common technicians in this field, they can obtain other attached figures. Based on these structures shown in the attached figure. without making additional creative endeavors.

DETAILED DESCRIPTION

Combined with the Attached Figure in the embodiments of the utility model, to clearly and completely describe the technical scheme of the embodiments of utility model. Obviously, only part of the embodiments of utility model (instead of all of the embodiment) are described here. Based on the embodiments of this utility model, all other embodiments acquired by the common technicians in this field without creative work, shall be in the protection scope of this utility model.

It should be noted that, if there is a directional indication (upper, lower, left, right, front, and rear, etc.) in the embodiments of the utility model, the directional indication is only used to explain the relative positional relationship, motion condition, etc. between the components in a particular position (as shown in the Attached Figure), and if the particular attitude is changed, the directional indication is changed accordingly.

In addition, if there are descriptions relating to "first", "second" and the like in the embodiments of the utility model, such descriptions of "first", "second" and the like are for descriptive purposes only and are not to be construed as indicating or implying their relative importance or implying an indication of the number of indicated technical features. As such, a feature that defines as "first", "second" may explicitly or implicitly include at least one of that features. In addition, the "and/or" as stated in the whole text should be understood as there are three paralleled schemes where scheme A, or scheme B or scheme A and scheme B can be met at the same time (taking "A and/or B as an example"). In addition, the technical schemes of embodiments may be combined with each other, but must be available for common technicians in this field, and when the combination of the technical scheme is contradictory or impossible, it should be considered that the combination of the technical scheme does not exist and not fall within the scope of the utility model.

Figure 1:
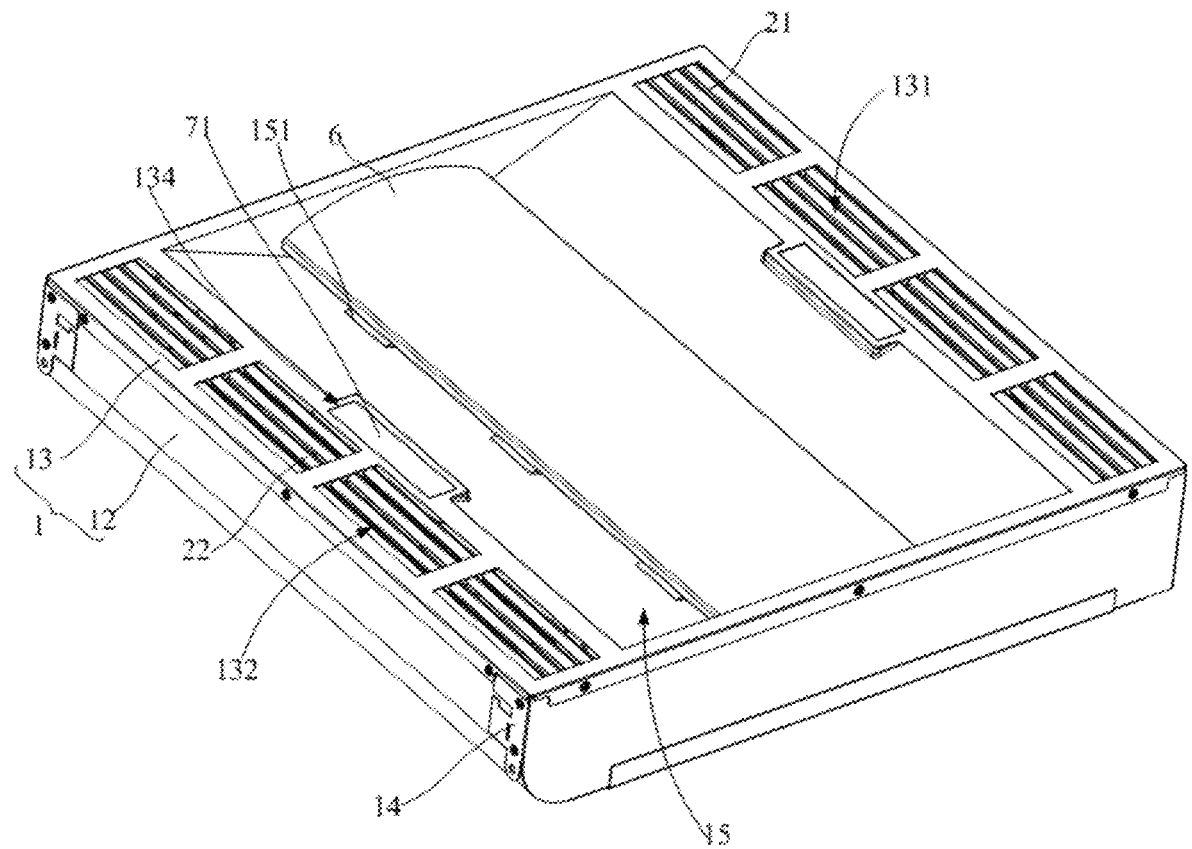
FIG. 1 is a schematic diagram showing the structure of an example of the germicidal panel light of the utility model.
Figure 2:
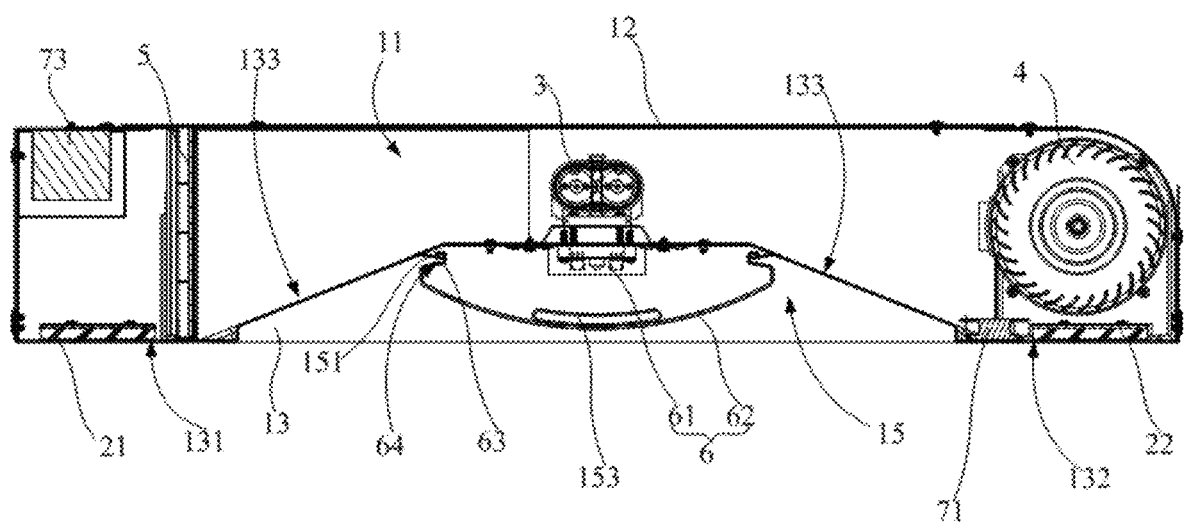
FIG. 2 is a schematic diagram showing the sectional structure of the germicidal panel light in FIG. 1.
Figure 5:
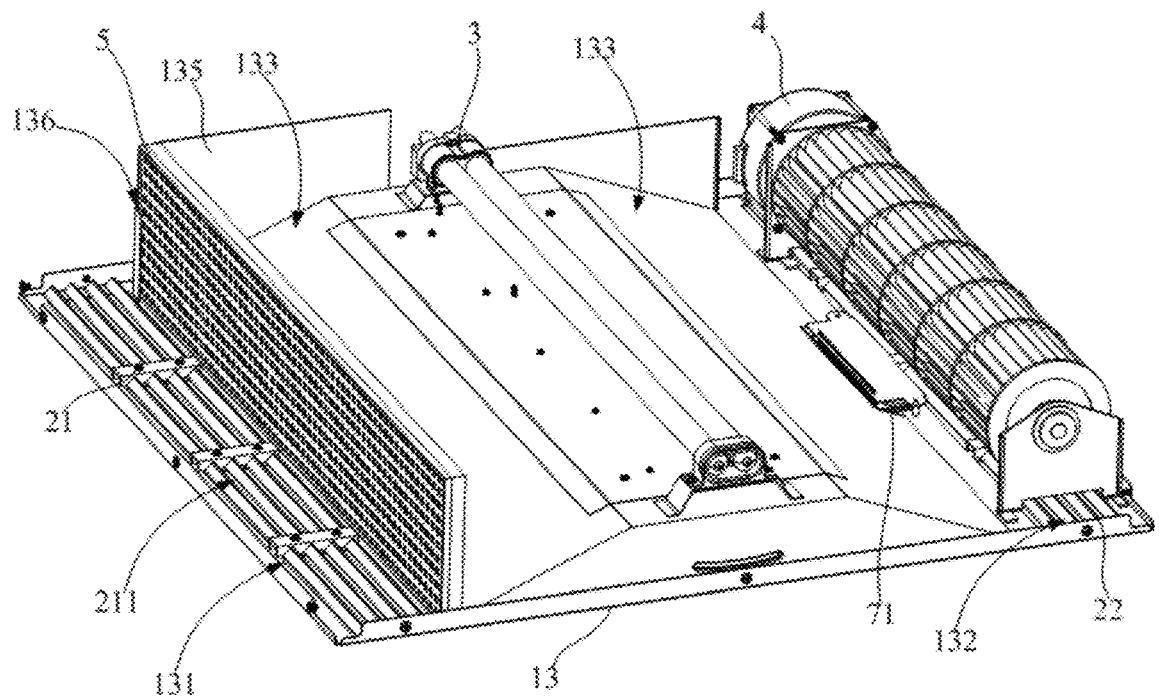
FIG. 5 is a schematic diagram showing the structure of the germicidal panel light in FIG. 4.
Figure 6:
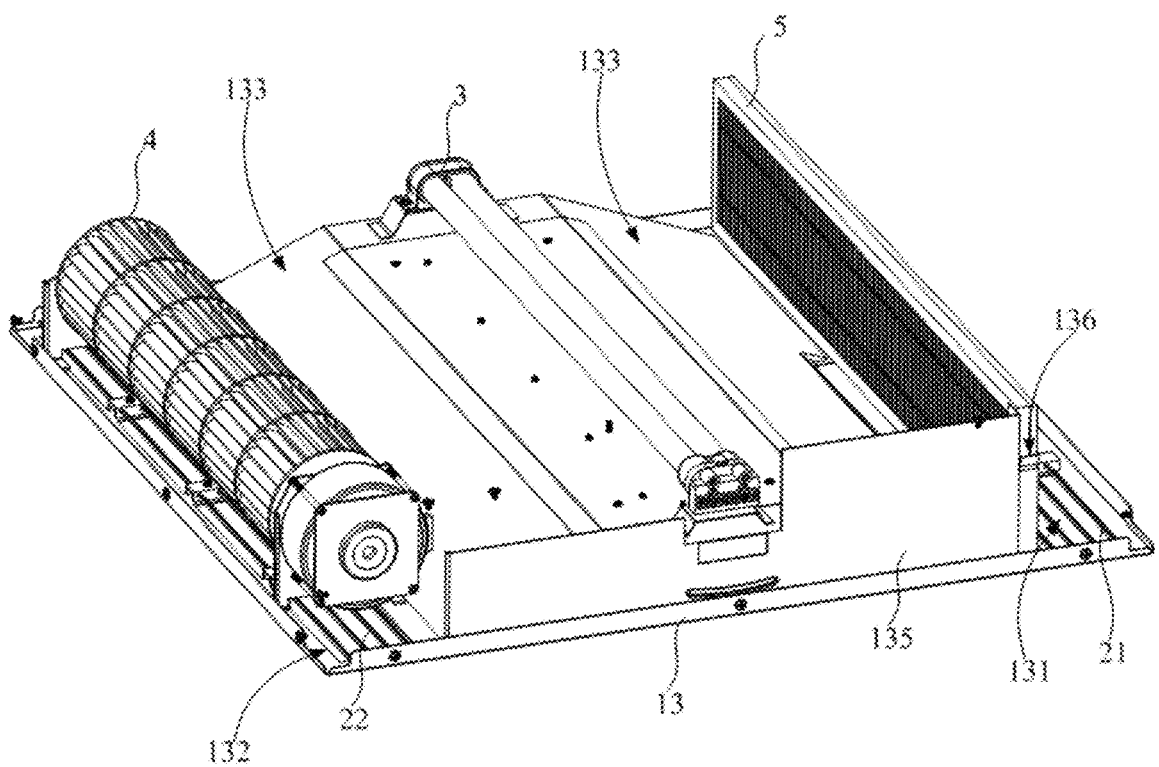
FIG. 6 is a schematic diagram showing the structure of another perspective of the germicidal panel light in FIG. 5.

The utility model discloses a germicidal panel light. FIG. 1 is a schematic diagram showing the structure of an example of the germicidal panel light of the utility model; Reference drawing 2 is a schematic diagram showing the sectional structure of the germicidal panel light in FIG. 1; Reference drawing 3 is the schematic diagram showing the assembly structure of germicidal panel light in FIG. 1; Reference drawing 4 is another schematic diagram showing the assembly structure of germicidal panel light in FIG. 1; Reference drawing 5 is a schematic diagram showing the structure of the germicidal panel light in FIG. 4; Reference drawing 6 is a schematic diagram showing the structure of another perspective of the germicidal panel light in FIG. 5; Reference drawing 7 is a third schematic diagram showing the assembly structure of germicidal panel light in FIG. 1; Reference drawing 8 is a partial enlarged FIG. of section A in FIG. 7; Reference drawing 9 shows a structural schematic diagram of lampshade in FIG. 7;

In the Embodiment of the utility model, as shown in FIG. 1, and combined with FIG. 2 FIG. 5 FIG. 6, the germicidal panel light includes: Housing 1, sterilization component 3, fan component 4, and lighting component 6. Taking the housing 1 as the mounting part, the sterilization component 3, the fan component 4 and the lighting component 6 are provided on the housing 1.

In the embodiment, the housing 1 is provided with the mounting cavity 11 as well as the air inlet 131 and the air outlet 132 connecting to the mounting cavity 11, the inner wall of the mounting cavity 11 is provided with the air guiding plane 133 respectively corresponding to the air inlet 131 and the air outlet 132, the appearance of the housing 1 is provided with the containing groove 15 whose inner wall is provided as a reflecting surface; the sterilization component 3 is provided in the mounting cavity 11; fan component 4 is provided in the mounting cavity 11 and is provided at intervals with the sterilization component 3; lighting component 6 is provided in the containing groove 15.

In the embodiment, the mounting cavity 11 as well as the air inlet 131 and the air outlet 132 connecting the mounting cavity are provided inside the housing 1, the fan component 4 and the sterilization component 3 are provided inside the mounting cavity 11 at intervals, and negative pressure is generated inside the mounting cavity 11, so that air enters the mounting cavity 11 from the air inlet 131 and exhausted from the air outlet 132. Wherein, an air guiding plane 133 nearby the air inlet 131 is formed on the inner wall of the mounting cavity 11, when air flows into the mounting cavity 11 from the air inlet 131, air is guided by the air guiding plane 133, so that air can flow into the mounting cavity slowly, which reduces noises generated. The equipment is characterized by large air volume but low noises. In the meanwhile, the air outlet 132 is provided with an air guiding plane 133 which can guide air out slowly, reducing generation of noises. In another aspect, the appearance of the housing 1 is provided with a containing groove 15 where the lighting component 6 is provided, so that the inner wall of the containing groove 15 reflects the ray of light of the lighting component 6 to recycle ray of light, a lighting area where the luminance is lower than the body of the lighting component 6 is formed in the containing groove, so that dazzle caused by the lighting component is reduced, the lighting quality of the germicidal panel light is improved, and the lighting cost is saved. In yet another aspect, the appearance of the housing 1 is provided with the containing groove 15 inside which the lighting component 6 is provided to reduce the height of the lighting component 6 out of the surface of the housing 1, reduce the overall thickness of the germicidal panel light and reduce the dimension of the germicidal panel light. In addition, the lighting component is provided in the containing groove, reducing the dimension of the lighting component and saving the cost of the lighting component; the lighting component is mounted from the front side. The process is simple and assembly is more convenient.

Optionally, according to FIG. 2, two air guiding planes 133 comprise the first plane provided corresponding to the air inlet 131 and the second plane provided corresponding to the air outlet 132.

In the embodiment, the first plane is provided by facing the air inlet 131. After flowing into the air inlet 131, air is guided by the first plane. Or, one end of the first plane connects to the periphery of the air inlet 131. After flowing into the air inlet 131, air is guided into the mounting cavity 11. In another aspect, the second plane is provided by facing the air outlet 132. When air is blown to the second plane, air is guided by the second plane and is blown out from the air outlet 132. Or, one end of the second plane connects to the periphery of the air outlet 132. After flowing into the mounting cavity 11, air is guided by the second plane to the air outlet 132.

Optionally, according to FIG. 2, the air guiding plane 133 nearby the air inlet 131 is provided in a tilt way from the air inlet 131 to the middle of the mounting cavity 11.

Optionally, according to FIG. 2, the air guiding plane 133 nearby the air outlet 132 is provided in a tilt way from the air outlet 132 to the middle of the mounting cavity 11

Optionally, the appearance of the housing 1 is any shape, such as rectangular cube, column, triangle cube, etc.; the appearance of the housing 1 can be any of other irregular shapes, such as animal shape, irregular polygon, etc.

In one embodiment of this utility model, the housing 1 is a rectangular cube. The mounting cavity 11 is provided in the housing 1. The air inlet 131 and the air outlet 132 connect to the mounting cavity 11 and the peripheral space of the housing 1. Understandably, the air inlet 131 or the air outlet 132 can be provided on any wall of the housing 1. For example, the air inlet 131 and the air outlet 132 can connect to different walls of the housing 1 respectively; or, the air inlet 131 and the air outlet 132 connect to one same wall of the housing 1, and the air inlet 131 and the air outlet 132 are provided at intervals.

Optionally, the air inlet 131 and the air outlet 132 connect the mounting cavity 11, forming an air duct. When the mounting cavity 11 is a long cavity, since the sterilization component 3 and the fan component 4 need to be provided inside the mounting cavity 11, the distance between the air inlet 131 and the air outlet 132 can be the length of the corresponding sterilization component 3 and the fan component 4. In another aspect, when the mounting cavity 11 is a bended cavity, mounting positions can be provided for the sterilization component 3 and the fan component 4 inside the mounting cavity 11, and the air inlet 131 and the air outlet 132 can be provided adjacently.

In one embodiment of this utility model, according to FIG. 2, the sterilization component 3 and the fan component 4 are provided at intervals. Wherein, the fan component 4 can be provided on one side of the sterilization component 3 departing from the air inlet 131; in other words, the fan component 4 is provided on one end of the mounting cavity 11 nearby the air outlet 132 to increase the distance between the fan component 4 and the air inlet 131. When the fan component 4 works, collision between the air flow generated in the periphery of the fan component 4 and the air flow generated at the air inlet 131 is reduced, so that noises can be reduced. In the meanwhile, the air outlet 132 is provided with an air guiding plane 133 which can guide the air flow generated by the fan component 4 to the air outlet 132, avoiding that the air flow blows onto the inner wall of the mounting cavity 11 vertically, avoiding the generation of air flow opposite to the fan component 4 and reducing noises.

Optionally, sterilization component 3 can be UV fluorescent tube; or, the sterilization component 3 can be a high-temperature sterilization module; or, the sterilization component 3 can be an ozone sterilization device.

Understandably, the sterilization component 3 is provided in the mounting cavity 11, by which the UV or ozone generated by the sterilization component 3 is blocked by the inner wall of the mounting cavity 11, avoiding damage to users caused by the UV or ozone and improving the safety and sterilization efficiency.

In one embodiment of this utility model, according to FIG. 1, FIG. 5 and FIG. 6, the germicidal panel light also comprises the air inlet grille 21 and the air outlet grille 22 connecting to the housing 1; the air inlet grille 21 covers the air inlet 131; the air outlet grille 22 covers the air outlet 132.

In the embodiment, the air inlet 131 is provided with the air inlet grille 21, so that partial air inlet grille 21 blocks the air inlet 131, the air inlet grille 21 can also be used for guiding the air flow to make the air flow slowly flows into the mounting cavity 11; in another aspect, the air outlet 132 is provided with the air outlet grille 22 blocking the air outlet 132 partially, by which the sounds generated by the fan component 4 cannot be directly transferred to the housing 1, and the air outlet grille 22 can also be used for guiding the air flow, so that the air flow can be blown out slowly, reducing noises.

Optionally, the air inlet grille 21 and the air outlet grille 22 can connect to the housing 1 in the fixed or dismountable way. In other words, the air inlet grille 21 and the air outlet grille 22 can connect to the housing 1 with screws or through welding; or, the air inlet grille 21 and the air outlet grille 22 can connect to the housing 1 with a spout.

In one embodiment of this utility model, according to FIG. 5, the air inlet grille 21 is provided with several air guiding vents 211, and the air incoming direction of each air guiding vent 211 faces the air guiding plane 133 of the nearby air inlet 131. In other words, the air inlet grille 21 comprises several flow guide bars which are provided at intervals, and each of these flow guide bars is parallel to the air guiding plane 133, so that air flowing into the mounting cavity 11 can be guided by the flow guide bar and go through the air guiding plane 133 slowly, reducing noises.

Optionally, the structure of the air outlet grille 22 is the same as that of the air inlet grille 21.

Understandably, the air outlet grille 22 is also provided with several air guiding vents whose air incoming direction is corresponding to the air guiding plane 133 nearby the air outlet 132. In other words, air flow guided by the air guiding plane 133 can be blown out from the air guiding vent on the air outlet grille 22, enabling air to flow slowly and reducing noises.

Optionally, the air inlet 131 and the air outlet 132 are provided at intervals. Wherein, one end of one air guiding plane 133 is adjacent to the air inlet 131, and one end of another air guiding plane 133 is adjacent to the air outlet 132, and the extended length of two air guiding planes intersects in the mounting cavity 11.

In one embodiment of this utility model, according to FIG. 5 and FIG. 6, the fan component 4 is provided corresponding to the air outlet 132, and the fan component 4 is a centrifugal fan. In other words, negative pressure is generated by the centrifugal fan, and then air flow is generated in the mounting cavity 11 to reduce noises. In another aspect, the centrifugal fan is provided at the air outlet 132, after air flow is generated in the periphery of the centrifugal fan, air flow is guided by the air guiding plane 133 and is blown out directly to reduce noise.

In the embodiment, the centrifugal fan generates negative pressure, which can reduce the revolving speed and noises, compared with the axial flow fan; in the meanwhile, the centrifugal fan can make better use of the space of the panel light, enabling the germicidal panel light to have a compact structure and saving the volume.

Optionally, the fan component 4 comprises a motor and a wind wheel, the fan connects to the inner wall of the mounting cavity 11 in a fixed way, the wind wheel connects to the motor, when the output shaft of the motor revolves, it drive the wind wheel to revolve to generate negative pressure, and then air flow is generated in the mounting cavity 11.

Figure 4:
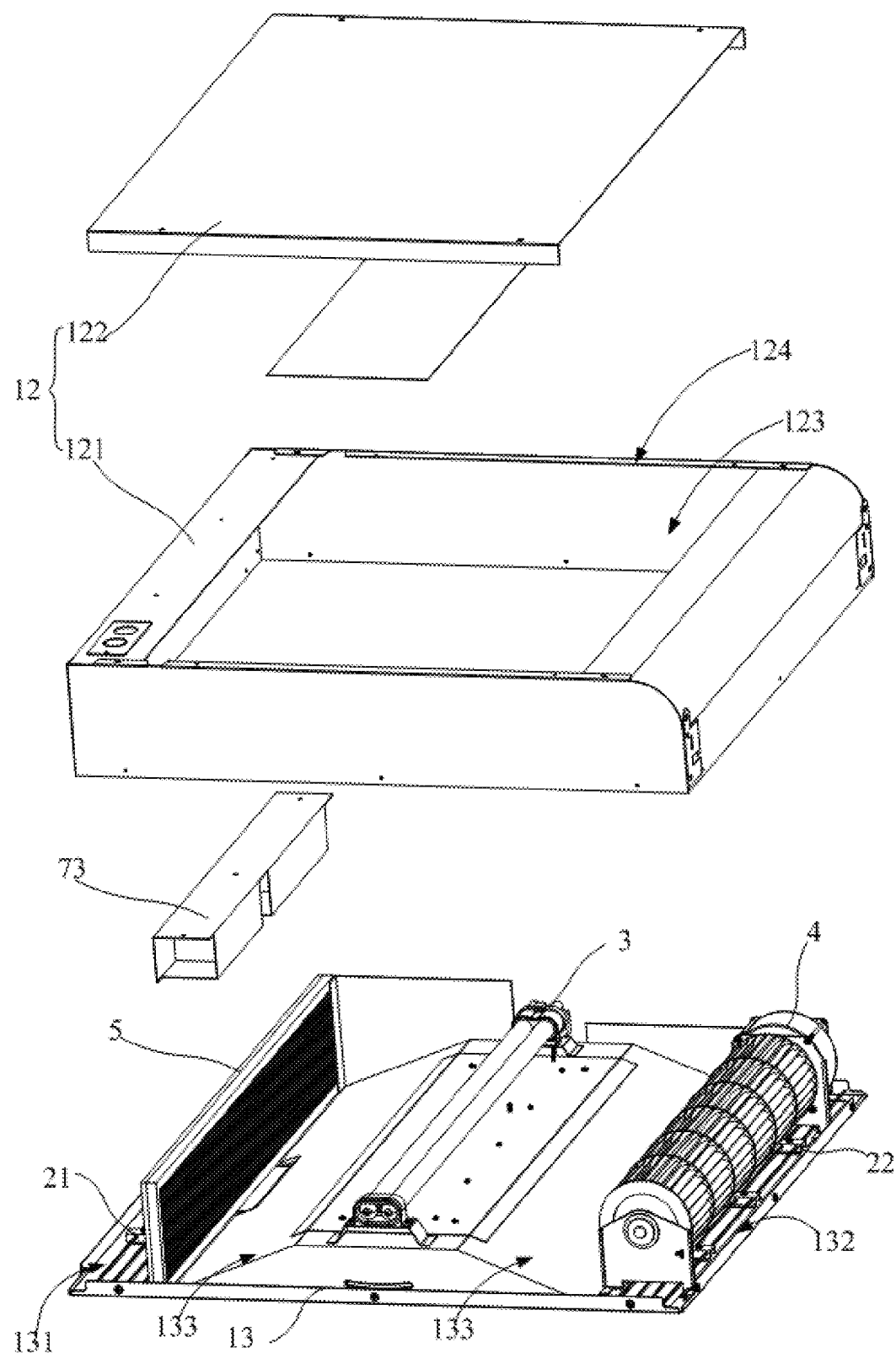
FIG. 4 is another schematic diagram showing the assembly structure of the germicidal panel light in FIG. 1.

In one embodiment of this utility model, according to FIG. 2 and FIG. 4, the air inlet 131, mounting cavity 11 and air outlet 132 cooperate to form an air duct; the germicidal panel light also comprises the filter component 5 connecting to the inner wall of the mounting cavity 11, the filter component 5 covers the air duct and is provided nearby the air inlet 131.

In the embodiment, the filter component 5 is provided in the mounting cavity 11 and covers the air duct, so that the filter component 5 filters air. In other words, air flows into the mounting cavity 11 from the air inlet 131 and flows out of the air outlet 132, during which air is filtered by the filter component 5 to reduce suspended matters in the air. In another aspect, the filter component 5 has a honeycomb-shaped plane on which there are holes which can absorb or reflect noises generated by the fan component 4, further reducing noises generated by the germicidal panel light.

Optionally, the filter component 5 can be locked in the mounting cavity 11 with screws. Or, a locating groove can be provided in the mounting cavity, and the periphery of the filter component 5 is snap-fitted with the locating groove.

In one embodiment of this utility model, according to FIG. 2 and FIG. 4, the sterilization component 3 is a UV fluorescent tube; the inner wall of said mounting cavity 11 is provided as a reflecting surface.

In the embodiment, the inner wall of the mounting cavity 11 is provided as a reflecting surface, so that it can reflect UV generated by the UV fluorescent tube, and then UV irradiates air in the mounting cavity 11 for several times, improving the sterilization effect.

In one embodiment of this utility model, two mirror structures can be provided on the inner wall of the mounting cavity 11, and two mirror structures connect to the inner wall of the mounting cavity 11 in a fixed way and are on both sides of the sterilization component 3.

In one embodiment of this utility model, the inner wall of the mounting cavity 11 can be coated with reflective materials to form a reflecting surface on the inner wall of the mounting cavity 11.

In one embodiment of this utility model, a reflecting surface can be formed on the inner wall of the mounting cavity 11 in the way of metal deposition or electroplating.

In one embodiment of this utility model, according to FIG. 1, the germicidal panel light also comprises several lifting lugs 14 which connect to the peripheral wall of the housing 1.

In the embodiment, the periphery of the housing 1 is provided with several lifting lugs 14, so that the germicidal panel light is hung on the wall.

Optionally, the lifting lug 14 is a metal part where there is a through-hole. The metal part can be a plane structure and is locked to the housing 1 with screws. The lifting lug 14 can be concealed. When lifting lug 14 is needed for suspending the germicidal panel light, the metal part can be bended to form the first part connecting to the housing 1 and the second part out of the periphery of the housing 1. The second part is provided with through-holes. When lifting lug 14 is not needed, lifting lug 14 is closed to the peripheral wall of the housing 1, reducing the volume of the panel light and facilitating packaging and transport of the product. Compared with the convex lifting lug structure of conventional panel lights, the concealed design of lifting lug 14 of the utility model can also prevent lifting lug 14 being collided during the transport.

Figure 3:
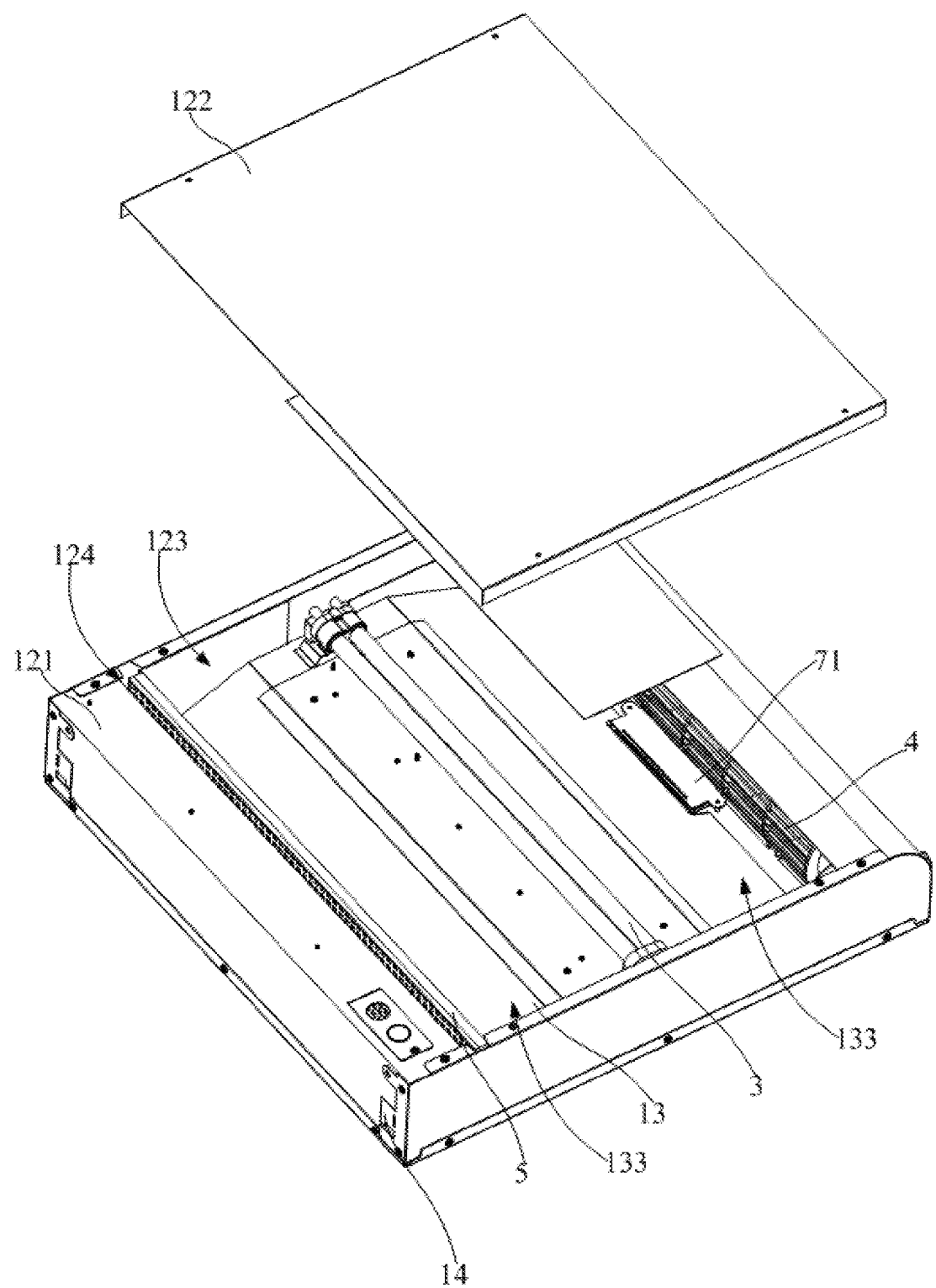
FIG. 3 is a schematic diagram showing the assembly structure of the germicidal panel light in FIG. 1.

In one embodiment of this utility model, according to FIG. 1, FIG. 2 and FIG. 3, the housing 1 is also provided with the mounting hole 134 which is provided at intervals with the air inlet 131, the air outlet 132 and the containing groove 15; the germicidal panel light also comprises the display module 71 which is provided in the mounting cavity 11 and corresponding to the mounting hole 134.

In the embodiment, according to FIG. 2 and FIG. 4, the germicidal panel light also comprises the control component 73 which is installed in the mounting cavity 11. The control component 73 comprises the main control circuit board and the power supply. Wherein, the main control circuit board connects electrically to one or several component/s of the sterilization component 3, the lighting component 6 and the fan component 4 to achieve the working status of the sterilization component 3 and the fan component 4. The display module 71 connects electrically to the main control circuit board of the germicidal panel light and cooperates with the main control circuit board to display the working status of the sterilization component 3 and the fan component 4. The control component 73 can control and adjust the sterilization component, the fan component and the lighting component with the help of an external remote controller.

Optionally, the display module 71 can comprise a flexible circuit board and a display screen, and the display screen connects electrically to the main control circuit board through the flexible circuit board.

In one embodiment of this utility model, according to FIG. 1, FIG. 2 and FIG. 4, housing 1 comprises the bottom housing 12 and the front housing 13 which connect to each other and form the mounting cavity 11 in the way of enclosure, the front housing 13 is provided with the air outlet 132 and the air inlet 131 which are provided respectively on the near side of two facing sides of the front housing 13, the middle of the front housing 13 sinks towards the mounting cavity 11, forming two air guiding planes 133 and the containing groove 15; the sterilization component 3 and the fan component 4 connect to the front housing 13 and/or the bottom housing 12.

In the embodiment, the bottom housing 12 and the front housing 13 are provided separately to facilitate mounting/dismounting of the germicidal panel light and improve the assembly efficiency.

Optionally, the bottom housing 12 can be provided with the mounting groove 123; Front housing 13 connects to the bottom housing 12, and covers the notch of mounting groove 123, forming the mounting cavity 11 in the way of enclosure. The front housing 13 is provided with the air outlet 132 and the air inlet 131 which are provided respectively on the near side of two facing sides of the front housing 13, the middle of the front housing 13 sinks towards the mounting cavity 11, forming two air guiding planes 133 and the containing groove 15;

In the embodiment, the middle of the front housing 13 sinks towards the mounting cavity 11, forming two air guiding planes 133 and the containing groove 15, and the front housing 13 can be produced in the way of extrusion forming, which can reduce the fabrication procedure of the front housing 13, effectively reduce the mounting procedure and save the cost.

Optionally, the filter component 5 connects to the bottom housing 12 and/or the front housing 13, covers the air duct and is provided nearby the air inlet 131.

Optionally, according to the FIG. 5 and the FIG. 6, one surface of the front housing 13 facing the bottom housing 12 is provided with a metal locating part 135 which is provided nearby the periphery of the front housing 13, so that the metal locating part 135 can be tightly close to the inner wall of the mounting cavity 11 when the front housing 13 and the bottom housing 12 are mounted. Wherein, the metal locating part 135 is provided with the locating groove 136 which is provided in the same direction as that from the front housing 13 to the bottom housing 12. The filter component 5 is provided in the locating groove 136 in the insertion way.

Optionally, the filter component 5 is locked with the metal locating part 135 via screws.

In one embodiment of this utility model, according to FIG. 3 and FIG. 4, the bottom housing 12 comprises the housing body 121 and the back housing 122, the housing body 121 is provided with the mounting groove 123 and the offsetting hole 124 connecting to the bottom wall of the mounting groove 123, the back housing 122 connects to the housing body 121 and covers the offsetting hole 124; the front housing 13 connects to the housing body 121 and covers the notch of the mounting groove 123.

In the embodiment, the back housing 122 and the housing body 121 are dismountable, when components inside the mounting cavity 11 break down, the back housing 122 can be opened for inspection and repair of the equipment by operators.

For example: the sterilization component 3 is a UV fluorescent tube, when the UV fluorescent tube breaks down, the back housing 122 can be opened to replace the UV fluorescent tube.

Figure 7:
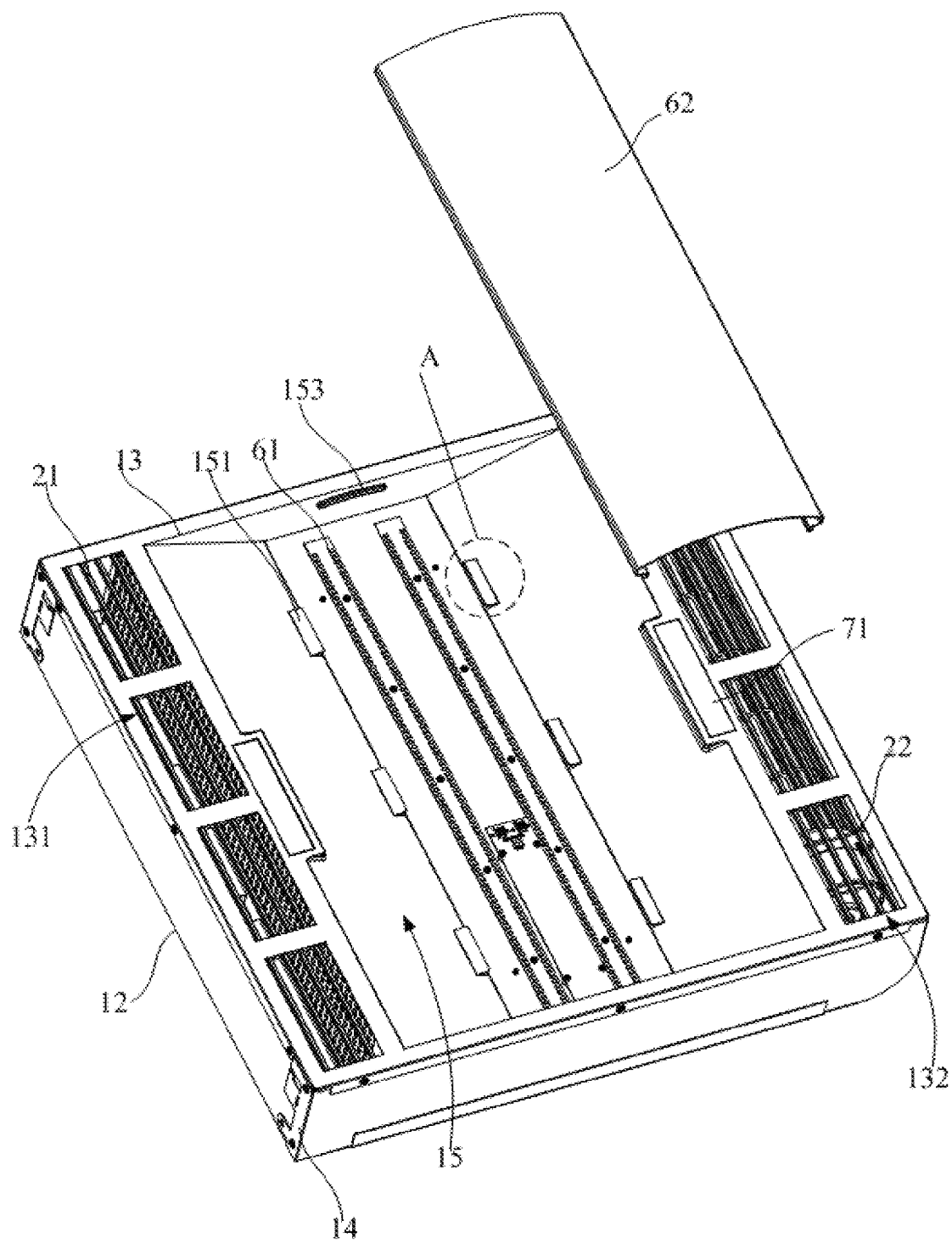
FIG. 7 is a third schematic diagram showing the assembly structure of the germicidal panel light in FIG. 1.
Figure 8:
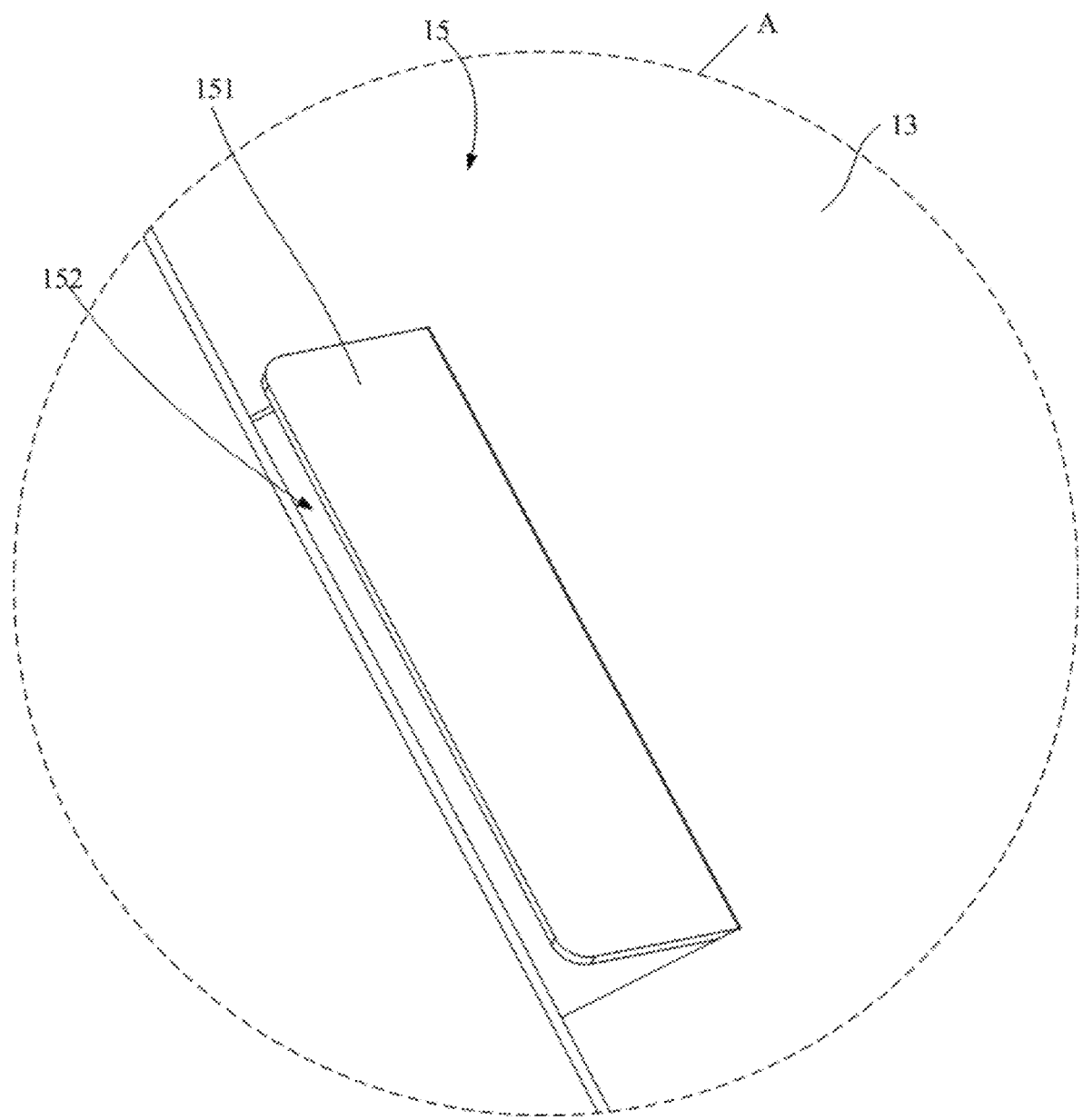
FIG. 8 is a partial enlarged FIG. of section A in FIG. 7.
Figure 9:
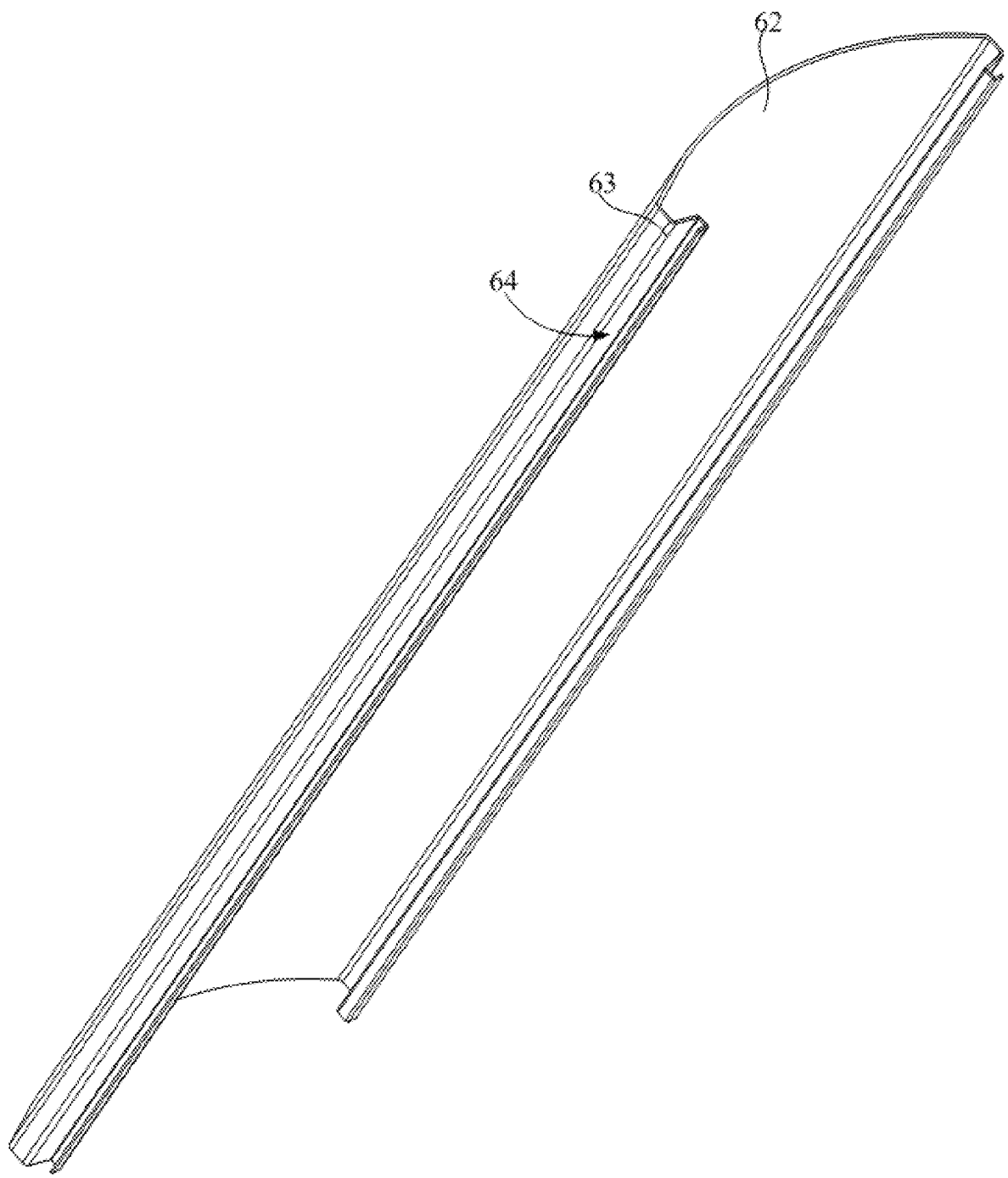
FIG. 9 shows a structural schematic diagram of lampshade in FIG. 7.

In one embodiment of this utility model, according to FIG. 7, FIG. 8 and FIG. 9, the containing groove 15 is uncovered, two facing side walls of containing groove 15 are provided with a convex part for locating 151, and each convex part for locating 151 works with the wall of containing groove 15, forming a snap slot 152 in the way of spacing;

the lighting component comprises the lighting module 61 and the lampshade 62, the lighting module 61 connects to the bottom wall of the containing groove 15 and is between two convex parts for locating 151, both sides of the lampshade 62 are provided with a fastening part 63, the fastening part 63 is contained partially in the snap slot 152 and works with the convex part for locating 151 for locating.

In the embodiment, the lampshade 62 and the housing 1 can be dismounted through the fastening part 63 and the convex part for locating 151, facilitating users to mount and dismount the lampshade 62 and inspect and repair the lighting module 61.

Optionally, two convex parts for locating 151 are provided nearby the bottom wall of the containing groove 15 and form the snap slot 152 with the bottom wall of the containing groove 15 in the way of spacing.

Optionally, the lighting module 61 is the LED light bar or the LED light bead. Wherein, the lighting module 61 connects electrically to the control component 73 of the germicidal panel light.

In one embodiment of this utility model, the lighting module 61 comprises two LED light bars which are provided in parallel.

Optionally, the wall of the mounting groove 123 can be provided with a mirror structure for reflecting the ray of light.

Optionally, the convex part for locating 151 should be at least one convex bar provided on the containing groove 15. The convex bar encloses the bottom wall or side wall of the snap slot 152, forming a snap slot 152.

Optionally, according to FIG. 7, the convex part for locating 151 comprises several convex bars which are provided on the side wall of the containing groove 15 in a line. The main body of the housing 1 of the germicidal panel light is made of metal plate, while convex part for locating 151 can be fabricated through press forming during the processing of the main body of the housing, enabling simple manufacturing process.

Optionally, according to FIG. 7, FIG. 8 and FIG. 9, the lampshade 62 is a metal plate structure of a convex arc, i.e. Lampshade 62 is a cambered structure. Both ends of the cambered metal plate structure are provided with a fastening part 63 respectively, and one side of each fastening part 63 back onto the other one is provided with the fastening slot 64. In other words, the cross section of the lampshade 62 is a sector. Two fastening parts 63 are on two ends of the sector. The lampshade 62 can be installed on the front side of the germicidal panel light, which can simplify the mounting process and improve the production efficiency.

Understandably, the surface of the front housing 13 back on to the housing 1 is the front side of the germicidal panel light.

Optionally, the lampshade 62 is made of plastics with processes of extrusion and cutting. Compared with the slab lampshade of other panel lights, this product is characterized by high light transmittance, good ductility and low cost. When the lampshade 62 connects to the housing 1, the convex part for locating 151 is contained in the fastening slot 64, and the fastening part 63 is contained partially in the snap slot 152; in other words, the fastening part 63 and the convex part for locating 151 are inserted into each other for locating. In the embodiment, the lampshade 62 is a cambered structure, so that the lighting module 61 disperses ray of light. In the meanwhile, it also facilitates users to press the lampshade 62 to make it be deformed elastically for dismounting.

In one embodiment of this utility model, according to FIG. 2, FIG. 7 and FIG. 8, the inner wall of the containing groove 15 is provided with two holding blocks 153 in the protruding way, connection of two holding blocks 153 and connection of two locating parts intersect, two holding blocks 153 are against the inner wall of the lampshade 62, improving the stability of mounting of the lampshade 62. In other words, the cross section of the lampshade 62 is a sector, and the holding blocks 153 are against the inner wall of the sector.

Understandably, two facing side walls of the containing groove 15 are provided with convex parts for locating 151, and the other two facing side walls are provided with holding blocks 153.

The said description is only the preferred embodiment of the utility model, and it is not for this reason that the patent scope of the utility model is limited. Any equivalent structural transformation made by using the description of the utility model and the attached FIG., or direct/indirect application in other related technical fields under the inventive concept of the utility model, is included in the patent protection scope of the utility model.

What is claimed is:

1. A germicidal panel light comprising:
   a housing comprises a bottom housing and a front housing, said front housing and said bottom housing connect to each other and enclose each other, forming a mounting cavity, said front housing is provided with an air outlet and an air inlet, said air outlet and said air inlet are provided adjacent to two facing sides of said front housing respectively, a middle part of said front housing sinks towards said mounting cavity, forming two said air guiding planes and a containing groove whose inner wall is provided as a reflecting surface; wherein
   the two air guiding planes comprise a first plane provided corresponding to the air inlet and a second plane provided corresponding to the air outlet;
   the air guiding plane adjacent to the air inlet is tilted from the air inlet to the middle of the mounting cavity;
   a sterilization component is provided in said mounting cavity and arranged between the two air guiding planes;
   a fan component is provided in said mounting cavity and on one end of the mounting cavity adjacent to the air outlet, and the fan component is provided corresponding to the air outlet;
   a lighting component provided in said containing groove, said lighting component comprises a lighting module and a lampshade, the cross section of the lampshade is a sector;
   a control component is installed in the mounting cavity, located in the upper part of the air inlet; and
   the mounting cavity and the containing groove are separated by three shared walls.

2. The germicidal panel light as in claim 1, further comprising an air inlet grille and an air outlet grille connecting to said housing;
   said air inlet grille covers said air inlet; and said air outlet grille covers said air outlet.

3. The germicidal panel light as in claim 2, wherein said air inlet grille is provided with several air guiding vents, and the air incoming direction of each of said air guiding vents faces the air guiding plane adjacent to said air inlet.

4. The germicidal panel light as in claim 2, wherein said fan component is a centrifugal fan.

5. The germicidal panel light as in claim 1, wherein said air inlet, said mounting cavity and said air outlet cooperate to form an air duct; and
   said germicidal panel light further comprises a filter component connecting to the inner wall of said mounting cavity, said filter component covers said air duct and is provided adjacent to said air inlet.

6. The germicidal panel light as in claim 1, wherein said sterilization component is a UV fluorescent tube; and
   the inner wall of said mounting cavity is provided as a reflecting surface.

7. The germicidal panel light as in claim 1, wherein said germicidal panel light further comprises several lifting lugs, and each of said several lifting lugs connects to the peripheral wall of said housing.

8. The germicidal panel light as in claim 1, wherein said housing is also provided with mounting holes which are provided at intervals with said air inlet, said air outlet and said containing groove; and
   said germicidal panel light further comprises a display module provided in said mounting cavity and corresponding to said mounting hole.

9. The germicidal panel light as in claim 1, wherein said sterilization component and said fan component connect to said front housing and/or said bottom housing.

10. The germicidal panel light as in claim 9, wherein said bottom housing comprises a housing body and a back housing, said housing body is provided with a mounting groove and offsetting holes connecting the bottom wall of said mounting groove, said back housing connects to said housing body and covers said offsetting hole; and
    said front housing connects to said housing body and covers a notch of said mounting groove.

11. The germicidal panel light as in claim 1, wherein said containing groove is uncovered, two facing side walls of said containing groove are provided with a convex part for locating, each of said convex parts for locating works with the wall of said containing groove, forming a locating groove; and
    said lighting module connects to the bottom wall of said containing groove and is between two said convex parts for locating, two sides of said lampshade are provided with a fastening part contained partially in said locating groove and cooperating with said convex parts for locating.

* * * * *